United States Patent [19]

Fenick

[11] Patent Number: 4,917,347
[45] Date of Patent: Apr. 17, 1990

[54] REFRACTORY DIE FOR MAKING PORCELAIN DENTAL PROSTHESIS AND A THERMAL CONDUCTING PIN FOR USE THEREIN

[76] Inventor: Thomas J. Fenick, Garwood Rd., Trumbull, Conn. 06611

[21] Appl. No.: 270,346

[22] Filed: Nov. 14, 1988

[51] Int. Cl.⁴ ............................................. A61C 13/34
[52] U.S. Cl. ........................................ 249/54; 249/175; 249/177; 264/19; 433/74; 433/211; 433/213
[58] Field of Search ...................... 249/54, 61, 62, 134, 249/135, 175, 177; 264/16, 17, 18, 19; 433/74, 75, 194, 195, 211, 213

[56] References Cited

U.S. PATENT DOCUMENTS

| | | | |
|---|---|---|---|
| 3,153,283 | 10/1964 | Weissman | 433/74 |
| 3,521,354 | 7/1970 | Stern et al. | 433/74 |
| 3,931,677 | 1/1976 | Tinder | 433/74 |
| 4,001,938 | 1/1977 | Cooper | 433/74 |
| 4,129,281 | 12/1978 | Cooper | 433/74 |
| 4,205,443 | 6/1980 | Weissman | 433/74 |
| 4,371,339 | 2/1983 | Zeiser | 433/74 |
| 4,585,417 | 4/1986 | Sozio et al. | 433/222.1 |
| 4,591,385 | 5/1986 | Pearsall | 264/16 |
| 4,721,464 | 1/1988 | Roden et al. | 433/74 |

*Primary Examiner*—James C. Housel
*Attorney, Agent, or Firm*—Arthur T. Fattibene

[57] ABSTRACT

Phosphate bonded investments with solid high temperature dowels or pins for the preparation or making of all porcelain dental prosthetic restorations. More specifically, the solid, high temperature pin type dowels, when used in dies and models formed of phosphate bonded investment material for making porcelain restorations, when fired to a range between 1600°–2200° F. functions as a heat sink to effect a more uniform heating and cooling of refractory model and porcelain restoration thereon so that the form and shape of the vitrified porcelain restoration may be more accurately maintained.

2 Claims, 1 Drawing Sheet

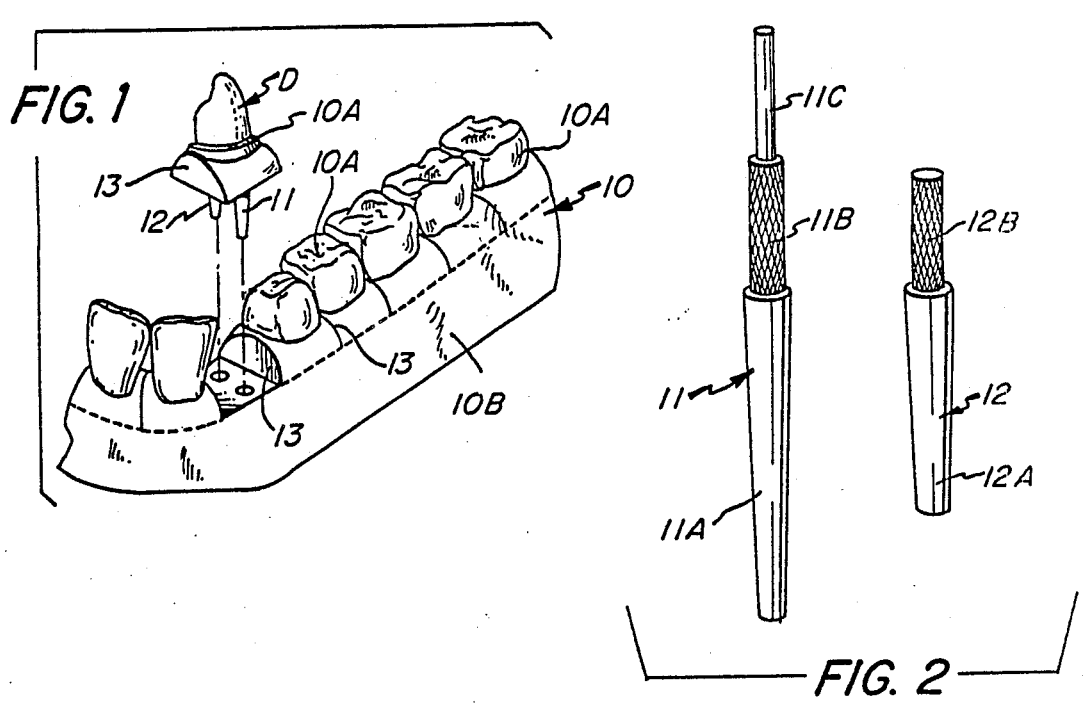
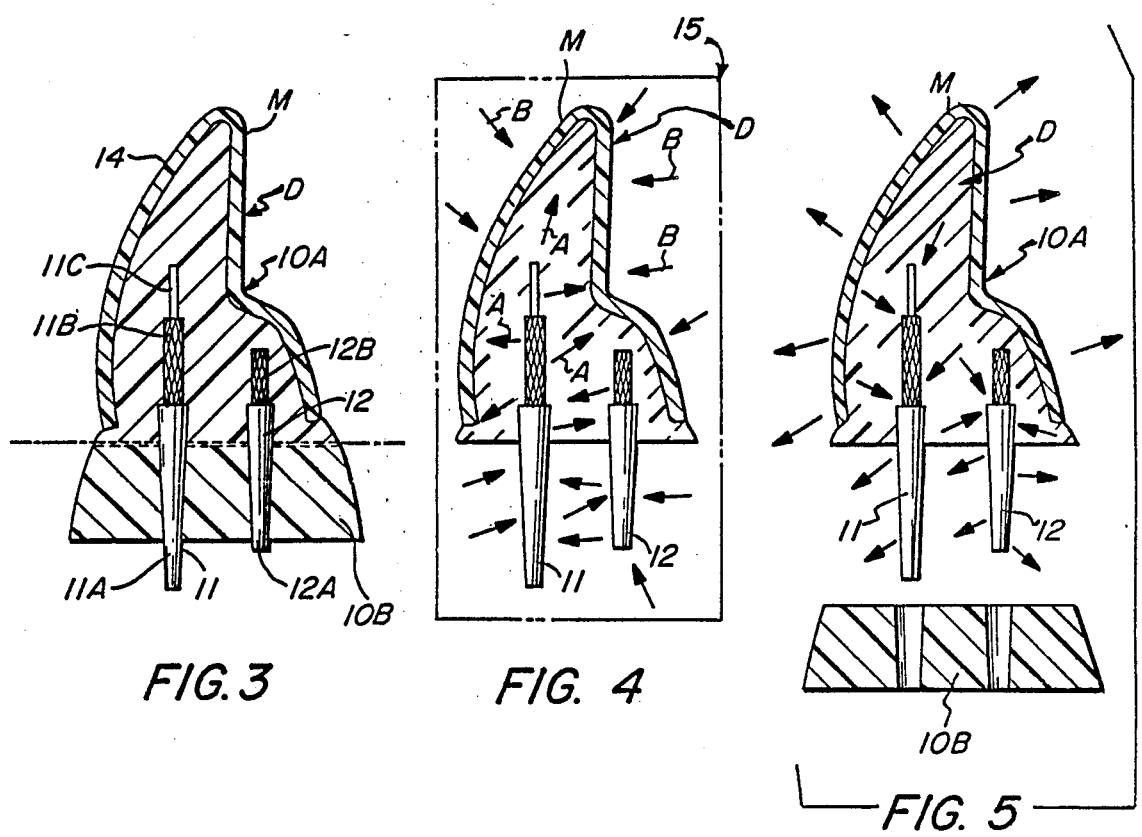

REFRACTORY DIE FOR MAKING PORCELAIN DENTAL PROSTHESIS AND A THERMAL CONDUCTING PIN FOR USE THEREIN

RELATED APPLICATIONS

This application is a divisional application of Applicant's pending application Ser. No. 055,915 filed June 4, 1987 for A Process of Forming All Porcelain Dental Prosthesis and Thermal Conducting Pin for use therein, now U.S. Pat. No. 4,834,651 granted May 30, 1989.

FIELD OF INVENTION

This invention is directed to the making of all porcelain dental prosthetic restorations.

BACKGROUND OF THE INVENTION

Heretofore, porcelain type dental prosthetic restorations, such as used for crowns, bridges and the like, comprised a restoration consisting of a metallic form or cast which was veneered with a porcelain coating or layer. The metal cast was generally formed of metal such as gold, silver, platinum and/or alloys thereof. Subsequently, the metallic cast portion of a porcelain restoration was made from less expensive base metal alloys of chrome, cobalt, nickel or the like, to which the porcelain was applied and thereafter fired to vitrification under vacuum at temperatures ranging between 1600°–2200° F. While the metal based porcelain restorations were effective, all porcelain restorations are esthetically preferable. However, the forming of all porcelain restorations presented a number of problems distinct from those encountered in making the metal-porcelain restorations.

The making of all porcelain restorations required the making of a die or mold of a suitable refractory material that could withstand the firing temperatures at which porcelain is required to be vitrified. A serious problem heretofore encountered with making all porcelain restorations was the difference in the thermal coefficient of expansion of the refractory material of the die and the porcelain material. This difference in the relative expansion and contraction rate upon heating and cooling of the die or mold and the porcelain cause the porcelain to either separate from the die and/or crack, thereby rendering the predictability of attaining a properly fitting porcelain restoration very uncertain. The problem in achieving a properly fitting all porcelain restoration was further aggrevated when a multiple tooth porcelain restoration was required, e.g., a bridge.

Because of the cracking and/or separation of the porcelain from the die or mold, it was heretofore necessary to effect the necessary repairs after firing and then refire the porcelain. Consequently, with the prior known techniques, repeated repairs and refirings were required. Oftentimes, as many as four, five or more firings were required before a satisfactory all porcelain restoration was achieved. Such numerous firings necessarily increased the overall cost, time and labor involved to fabricate a satisfactory all porcelain restoration.

To obviate some of the problems encountered in making all porcelain type restorations, there is disclosed in U.S. Pat. No. 3,453,736 the concept of utilizing hollow dowels or pins to compensate for the difference of thermal expansion encountered in making all porcelain restorations. It was also noted in this patent that the use of solid pins or dowels was not desirable, as such pins would stress and fracture the refractory die or mold during firing. However, the concept described therein has not, to my knowledge, achieved commercial acceptance and it is not known to be widely used or in use.

It is also known that dowel pins have been widely used in making stone dies or molds, which are not subject to firing or used in making porcelain restorations. Dowels used for making stone dies or molds, which are not subjected to high temperatures, are generally formed of plastic or low temperature materials. An example of such dowel as used in a non-firing die or mold is evidenced in U.S. Pat. No. 4,139,943 granted Feb. 20, 1979.

Other examples of pins, posts or dowels as used in various dental procedures, which are not considered to be related to the making of porcelain restorations, are evidenced by U.S. Pat. Nos. 1,639,782; 1,867,300; 3,153,282; 3,541,688; 4,174,570; 4,398,884; 4,443,192; and 4,449,931.

OBJECTS

An object of this invention is to provide a technique for forming porcelain dental prosthetic restorations which is relatively simple and positive in operation.

Another object is to provide for making a satisfactory all porcelain dental prosthetic restoration in a minimum number of firings.

Another object of this invention is to fabricate a die or mold of a phosphate bonded investment and having disposed therein a thermal conducting pin or pins for uniformly distributing the heat therethrough on heating and cooling.

Another object of this invention is to provide a specifically constructed pin or dowel that will optimize the distribution of heat through the die or mold and the porcelain material thereon in a manner that will minimize cracking and/or separation of the porcelain from the die at the interface thereof.

SUMMARY OF THE INVENTION

The foregoing objects, features and other advantages are attained by forming a die or mold, in preparation of forming an all porcelain restoration, of a phosphate bonded investment which includes a silicate filler and magnesium oxide mixed with ammonia and water. The phosphate bonded investment, when mixed, is poured into the wax or rubber impression which has been formed of a patient's teeth. Prior to the setting of the investment material, a pair of thermal conducting pins are inserted in the mold material. After the mold material has set, a second pour is made to form a base for the die mold, the base forming material being poured about the pins or dowels extending beyond the die. Prior to pouring the base material, the interface and pin extension are suitably lubricated or coated so as to render the pins readily releasable from the base material.

The dowel pins are specially constructed from high temperature metals which are structured so as to function as a heat sink for effecting generally uniform heating and cooling of the refractory material and the porcelain material. Preferably, each die or tooth configuration is provided with a matched pair of pins. The respective pins or dowels include an extended base portion which is slightly tapered inwardly toward its free end which extends into the mold base. The intermediate or other portion adapted to extend into the mold or die is serrated to provide a mechanical bond between the die and the pin. At least one of the matched pair of pins is provided with an extended portion arranged to transmit heat to a tip end of the die or mold. The arrangement is such that when a particular die or mold is fired to vitrify the porcelain thereon, that the dowel or pin will effect uniform heating and cooling of the die and porcelain thereon, whereby the mass of the pin effectively transmits the heat to and from the interior of the die in a rapid and uniform manner.

FEATURES

A feature of this invention resides in the provision of utilizing a phosphate bonded investment in conjunction with thermal conducting pins in fabricating the dies or mold on which an all porcelain dental prosthetic can be formed in a minimum of firings.

Another features resides in the specific construction of solid high temperature dowels or pins for use in a die or mold for making porcelain dental prosthetics.

Other features and advantages will become more readily apparent when considered in view of the drawings and specifications in which:

FIG. 1 is a partial prospective view of a mold or die formed of a phosphate bonded investment for making all porcelain dental prosthetic restorations.

FIG. 2 is a perspective view of a matched pair of thermo conducting pins of this invention.

FIG. 3 is a detail sectional view through a single die mold.

FIG. 4 is a schematic view of a die embodying the invention during a firing operation.

FIG. 5 is a schematic view of the die mold of FIG. 4 during a cooling thereof.

DETAILED DESCRIPTION

Referring to the drawings, there is shown in FIG. 1, the mold or die construction for making an all porcelain dental prosthetic in accordance with this invention.

Referring to the drawing, there is shown therein a model or die 10 formed of a phosphate bonded investment embodying the invention. It will be understood that the mold or die is formed by first mixing a slurry of phosphate bonded investment which comprises a phosphate material with a silicate filler and magnesium oxide, ammonia and water. Such phosphate bonded investment is of the type which is sold under the name Austenal Inlay Investment, product no. 2410-06, manufactured by Austenal International Co.

The slurry so formed is poured into a wax or rubber impression of a patient's teeth, which has been previously prepared by a dentist or a lab technician in the manner well known in the art.

With the phosphate investment bonded material placed in the wax or rubber teeth impression, a pair of thermo-conducting pins are placed in the slurry mix before it has fully set within the wax or rubber teeth impression.

Referring to FIG. 2, the pin or dowels 11 and 12 are formed as matched pairs, each of which are formed as a solid pin of a high temperature resistant material such as stainless steel, and more specifically 303 stainless steel or the like, which can withstand temperatures of at least 2200° F. with a minimum of oxidation and/or deterioration. As shown, pin 11 includes a tapered lower end portion 11A, which tapers inwardly toward the free end thereof. Intermediate the ends of pin 11 there is provided a knurled intermediate portion 11B. Beyond the end of the knurled portion 11B there is provided an extension or extended portion 11C. As noted, the intermediate portion 11B and the extended portion 11C are each provided with a progressively reduced cross-sectional area.

The other pin 12 of the matched pair comprises a relatively shorter pin which comprises a similar tapered lower end portion 12A which is somewhat shorter than taper portion 11A of pin 11 and an upper portion 12B which is knurled as indicated. The knurled portions 11B and 12B of the respective pins 11 and 12 provide the means whereby the phosphate bonded investment of the mold or die representing the formed tooth model 10A may be mechanically bonded to the respective pins or dowels upon curing. In accordance with this invention, a pair of matched pins 11 and 12 are inserted into a slurry mix placed in the wax or rubber impression so that the tapered end portions of the respective pins project beyond the surface of the phosphate investment that is poured into the impression.

Upon the curing of the phosphate bonded investment within the impression mold, the surfaces of the extended pin portions and the surface of the cured investment are lubricated or coated and a second pour is made to form the base 10B for the teeth mold or dies 10A. As best seen in FIG. 3, the second pour which defines the base 10B is poured to a level where the tapered end of the respective pins project slightly beyond the surface which forms the bottom of the base 10B.

As shown in FIGS. 3 to 5, the longer of the pins, e.g. pin 11, is inserted into the tooth die so that the extended portion 11C extends toward the high point of the tooth die, whereas the shorter pin 12 is disposed in the bulk or base portion of the tooth die.

When the second pour or base portion 10B has cured, the molded refractory or phosphate investment mold is removed from the impression mold. Thereafter, the individual teeth die, or group of teeth die, are severed or cut as indicated at 13 whereby one or more teeth die can be readily separated from the base 10B of the mold; as seen in FIG. 1.

It will be understood that the tooth or teeth to be restored by an all porcelain prosthesis restoration had been prepared by a dentist before the tooth impression was made. Thus, the die of the tooth to be restored upon the removal thereof from the wax impression is readied for receiving the coating of porcelain material. The die D, which is the replica of the treated tooth to be restored with an all porcelain restoration, is provided with a layer of porcelain material 14. In the illustrated embodiment, an all porcelain cap is shown.

The die or group of teeth die which define the mold for the porcelain restoration is then coated with the raw porcelain material M as best indicated in FIGS. 3 to 5. The die or group of teeth die so coated with the raw porcelain material is then placed in a kiln, oven or heater 15 and is subjected to a temperature ranging between 1800° to 2200° F., under a vacuum, so as to effect vitrification of the porcelain layer M.

As shown in FIG. 3, the provision of the high temperature dowel pins 11 and 12 function as a heat sink for conducting heat to the interior of the refractory die during a firing operation as indicated by arrows A. Simultaneously, the die D with the porcelain layer M thereon is being heated externally as indicated by arrows B. The arrangement is such that the internal surfaces of the die or mold D is being heated at substantially the same rate that the external surfaces of the porcelain layer M is being vitrified. Thus, the temperature of the die and the porcelain is being brought up to temperature in a substantially optimum uniform manner so as to resist any cracking or separation of the porcelain layer M.

Also, on cooling, the thermo conducting pins 11 and 12 tend to effect uniform cooling of the refractory die D and the vitrified layer of porcelain thereon. The pins 11 and 12 thus control the cooling down of the refractory die at substantially the same rate as the cooling of the vitrified porcelain. The functioning of the pins 11 and 12 as a heat sink to effect the uniform heating and cooling of the refractory die D and porcelain coating M thereon, effectively enables the vitrified porcelain prosthetic to resist cracking and/or separating from its die D. In this manner, the number of firings otherwise required to construct a satisfactory all porcelain restoration is reduced to a minimum of possibly one or two firings, as distinguished from four, five or more firings required by the prior known techniques.

From the foregoing, it will be noted that a refractory die D formed of an ammonia phosphate bonded investment material having a silicate filler in the presence of magnesium oxide, when used in conjunction with solid thermo conducting pins in the manner herein set forth, results in surprisingly reducing the number of firings otherwise required to form a satisfactory all porcelain prosthetic dental restoration. By effecting the reduction in the number of firings otherwise required, a more economical restoration is achieved as the cost of time, labor and effort is substantially reduced.

While the invention has been described with respect to the illustrated embodiment herein, it will be understood and appreciated that variations and modifications can be made without departing from the spirit or scope of the invention.

What is claimed is:

1. A refractory die for making a porcelain dental prosthetic restoration comprising a die simulating the shape of a prepared tooth which is adapted to receive a porcelain restoration, said die being made of an ammonia phosphate bonded investment, a solid high temperature pin imbedded in said refractory die for withstanding temperatures in the range of 1600° F. to 2200° F., with a minimum of oxidation, said pin having opposed end portions, one end portion of said pin projecting out of said refractory die material, and the other end portion being imbedded in said die whereby said pin during vitrification functions as a heat sink for conducting heat to and from the interior of the refractory die so that the internal area of the die is being heated and cooled at substantially the same rate as a layer of procelain adapted to be formed thereon.

2. A thermal conducting dowel pin for use in a refractory die for making a porcelain restoration, said dowel pin comprising a solid pin having opposed ends and formed of a high heat resistant material capable of withstanding temperatures in the range of 1600° F. to 2200° F. with a minimum of oxidation, said pin including a lower taper portion having a free end, a knurled portion connected to said taper portion opposite said free end and extendable into a refractory die, said taper portion being tapered inwardly from said knurled portion toward the free end thereof, said knurled portion having across sectional area which is less than the maximum diameter of the tapered portion, and an extended portion connected to said knurled portion opposite said taper portion and having a cross sectional area which is less than the cross sectional area of said knurled portion, said extended portion having a length which is adapted to be rendered wholly imbedded within a refractory die, said pin functioning as a heat sink to conduct heat to and from the interior of a refractory die.

* * * * *